United States Patent
Pagé

(10) Patent No.: US 6,815,462 B2
(45) Date of Patent: Nov. 9, 2004

(54) CARBOHYDRATE DERIVATIVES OF PACLITAXEL AND DOCETAXEL, METHOD FOR PRODUCING SAME AND USES THEREOF

(75) Inventor: Michel Pagé, Québec (CA)

(73) Assignee: Bioxel Pharma Inc., Sainte-Foy (CA)

( * ) Notice: Subject to any disclaimer, the term of this patent is extended or adjusted under 35 U.S.C. 154(b) by 59 days.

(21) Appl. No.: 10/338,856

(22) Filed: Jan. 9, 2003

(65) Prior Publication Data

US 2004/0138142 A1 Jul. 15, 2004

(51) Int. Cl.[7] .............................................. A61K 31/337
(52) U.S. Cl. ....................... 514/449; 549/510; 585/10
(58) Field of Search ........................... 514/449; 549/510

(56) References Cited

U.S. PATENT DOCUMENTS 5,981,564 A * 11/1999 Page et al. ................... 514/400
6,391,913 B1 * 5/2002 Page et al. ................... 514/449

* cited by examiner

*Primary Examiner*—Taofiq Solola
(74) *Attorney, Agent, or Firm*—Christian Cawthorn; Ogilvy Renault

(57) ABSTRACT

The invention relates to new carbohydrate derivatives of paclitaxel and docetaxel with increased solubility in water as compared to the parent compounds, paclitaxel and docetaxel These derivatives are produced from naturally occurring precursor molecules which upon hydrolysis yield these natural precursors and the original paclitaxel and docetaxel molecules. The present invention also relates to the composition and the use of such derivatives for cancer therapy. These derivatives may also be used in antifungal or antiviral therapy.

41 Claims, No Drawings

CARBOHYDRATE DERIVATIVES OF PACLITAXEL AND DOCETAXEL, METHOD FOR PRODUCING SAME AND USES THEREOF

TECHNICAL FIELD

The invention relates to carbohydrate paclitaxel and docetaxel derivatives to increase their solubility in water.

BACKGROUND OF THE INVENTION

Paclitaxel is a natural product extracted from the bark of the Pacific yew (*Taxus brevifolia*). It was thereafter found in other members of the Taxacae family including the yew of Canada (*Taxus canadensis*) found in Gaspesia, eastern Canada and *Taxus baccata* found in Europe whose needles contain paclitaxel and analogues and hence provide a renewable source of paclitaxel and derivatives. The crude extract was tested for the first time during the 60s and its active principle was isolated in 1971 by Wani et al. (Wani et al., *J. Am. Chem. Soc.* 93:2325–2327, 1971) who at the same time identified its chemical structure. It showed a wide range of activity over melanoma cells, leukemia, various carcinomas, sarcomas and non-Hodgkin lymphomas as well as a number of solid tumors in animals. Docetaxel is the active ingredient of Taxotere™ originally developed by Aventis Pharmaceuticals. It is prepared by semi-synthesis from 10-Deacetylbaccatin III, a taxane abundant in the European yew *Taxus baccata*. Taxotere is currently approved in the United States to treat patients with locally advanced or metastatic breast cancer after failure of prior chemotherapy and for treatment of non-small cell lung cancer. Clinical studies have shown that paclitaxel and docetaxel are very effective anti cancer agents. They are both microtubule blockers, but unlike other drugs inhibiting the mitosis by interaction with microtubules such as colchicin, vincristin and podophyllotoxin, paclitaxel and docetaxel do not prevent tubulin assembly. They rather accelerate the tubulin polymerization and stabilize the assembled microtubules. The drugs act in a unique way which consists in binding to microtubules, preventing their depolymerization under conditions where usually depolymerization occurred (dilution, calcium, cold and microtubules disrupting drugs). Paclitaxel and docetaxel block the cell cycle at prophase which results in an accumulation of cells in G2+M. Because of their unique structures and mechanism of action, paclitaxel and docetaxel were submitted to clinical trials. Interesting activity against many tumors, especially breast cancer and ovarian cancer refractory to chemotherapy, has been observed. However, because of its poor solubility in water, paclitaxel had to be administered in ethanol, Cremophor-EL and 5% sucrose diluted in saline or water. Cremophor-EL was responsible for hypersensitivity reactions observed in several patients (Rowinsky, E. K., et al., *J. Nat. Can. Inst.,* 82 (15), 1247–1259, 1990). Premedication with anti-histamines had to be administered in order to reduce the toxicity.

Poor solubility of paclitaxel constitutes an important limitation to its administration to cancer patients. To increase paclitaxel availability, total and partial syntheses have been reported. The improvement of paclitaxel solubility was obtained by adjunction of solubilizing functions such as carbonyl or sulfonyl groups with good results. Some of the synthesized products were more active than paclitaxel, many others had a biological activity equivalent or slightly inferior to that of paclitaxel while being far more soluble in water (Kingston. D. G., *Pharmacol. Ther.* (England), 52(1) p1–34, 1991). The complexity of the paclitaxel chemical structure rendered its total synthesis very difficult but it was achieved simultaneously by two different groups. However the yield of this synthesis of the order of 2–4% will have little impact on the paclitaxel availability (Borman, S., Total synthesis of anticancer agent paclitaxel was achieved by two different routes (Borman et al., 1994, *C & EN,* 21:32–4)).

Many attempts have been made to improve paclitaxel aqueous solubility with various components resulting in poorly stable products, inactive ones or derivatives which upon metabolism yielded undesirable side products. Moreover, sometimes the synthesis of these compounds required many chemical steps.

Paclitaxel has three hydroxyl groups at carbon 1, 7 and 2' susceptible of undergoing an acylation. Their reactivity varies according to the following order: 2'>7>>>1 (Mathew, A. E., et at., *J. Med. Chem.,* 35, 145–151, 1992). Acylation on C2' is the best way of paclitaxel modification because of its great reactivity, and because even if 2' acylpaclitaxels loose their property of promoting the microtubules polymerization in vitro, they are hydrolyzed in the cell and revert to paclitaxel and keep their cytotoxic activity (Kingston et al., 1990, *J Nat Prod,* 53:1–12; MELLADO, W., et al., *Biochem. Biophys. Res. Commun.,* 105: 1082–1089, 1984; Bicamumpaka C. and Page M. *Oncol Rep.* 1998 November–December 1998;5(6);1381–3; and Jaime J. and Page *M. Anticancer Res.* 2001 21(2A):1119–28.

Accordingly, to increase solubility, several derivatives have been synthesized by modification of the 2' or/and 7 hydroxyls. The 2' hydroxyl appears as a good candidate for chemical modification. The 7 hydroxyl requires more drastic conditions to react while the tertiary hydroxyl in position 1 is inert. The 2' and 7 hydroxyls have been modified by several groups (Deutsch, H. M., et al., *J. Med. Chem.,* 32: 788–792, 1989: Rose, W. C., et al., *Cancer Chemother. Pharmacol.,* 39: 486, 1997 and Bicamumpaka C. Page M. *Oncol Rep.* November–December 1998;5(6):1381–3. and Jaime J. and Page M. *Anticancer Res.* 2001, 21(2A) :1119–28), but only a few derivatives were synthesized with a sugar moiety as reported by Kingston et al. (Kingston, D. G. I., *Pharmac. Ther.,* 52: 1–34, 1991). However, many derivatives were insufficiently soluble, inactive or too unstable to be applied in a clinical situation.

Carbohydrates are very soluble in water and they are used by nature in the form of carbohydrate conjugates to eliminate some non-soluble metabolites.

It would be highly desirable to be provided with new active paclitaxel and docetaxel derivatives to increase the solubility of paclitaxel and docetaxel in water while, upon hydrolysis, and which derivatives produce non-toxic side products.

SUMMARY OF THE INVENTION

One aim of the present invention is to provide new paclitaxel and docetaxel derivatives modified at least at one of 2'- and 7 positions to improve their solubility.

Another aim of the present invention is to provide carbohydrate derivatives of paclitaxel and docetaxel which upon degradation yield non toxic carbohydrates and the original paclitaxel and docetaxel molecules.

Another aim of the present invention is to provide a method for the in vivo treatment or prophylaxis of cancer comprising the step of administering a therapeutically effective amount of a water-soluble paclitaxel or docetaxel derivative as defined above to a patient in need of such a treatment.

Another aim of the present invention is to provide a method for the in vivo treatment or prophylaxis of skin diseases comprising the step of applying topically a therapeutically effective amount of a water-soluble paclitaxel or docetaxel derivative as defined above to a patient in need of such a treatment.

In accordance with the present invention there are provided new paclitaxel and docetaxel derivatives or salts thereof having the following Formula I:

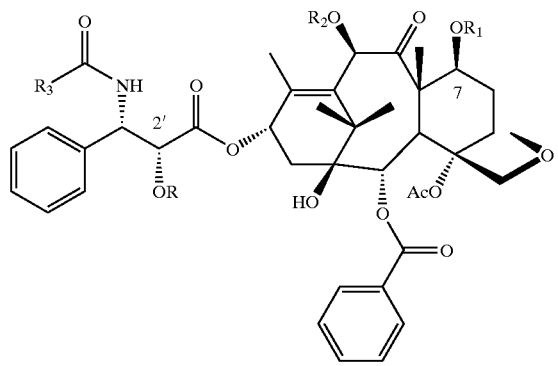

Wherein R and $R_1$, identical or different, are a hydrogen or CO—$(CH_2)_n$—CO—X in which n is 2 to 14 and X is a carbohydrate such as a monosaccharide, a disaccharide or a polysaccharide, an amino sugar or an amino acid and wherein $R_2$ is a hydrogen or acetyl and $R_3$ is phenyl (in the case of a paclitaxel derivative) or t-Butyloxy (in the case of a docetaxel derivative).

In one embodiment, R and $R_1$ interchangeably are a hydrogen and CO—$(CH_2)_n$—CO—X in which n is 2 to 14 and X is selected from the group consisting of D-glucosamine, D-galactosamine, mannosamine, fucosamine, lactosamine, mycosamine and muramic acid.

In a further embodiment, R and $R_1$, identical, are each CO—$(CH_2)_n$—CO—X in which n is 2 to 14 and X is selected from the group consisting of D-glucosamine, D-galactosamine, mannosamine, fucosamine, lactosamine, mycosamine and muramic acid.

In another embodiment, R and $R_1$ interchangeably are a hydrogen and CO—$(CH_2)_n$—CO—X in which n is 2 to 14 and X is a natural or synthetic polymer of amino sugars consisting of 2 to 100 units of D-glucosamine.

In still one embodiment of the invention, R and $R_1$ are each CO—$(CH_2)_n$—CO—X in which n is 2 to 14 and X is a natural or synthetic polymer of amino sugars consisting of 2 to 100 units of D-glucosamine. Preferably, the polymer of amino sugar is identical on R and $R_1$.

In a further embodiment, R and $R_1$ are interchangeably a hydrogen and CO—$(CH_2)_n$—CO—X in which n is 2 to 14 and X is a natural or partially digested chitosan. Preferably, R and $R_1$, identical, are each CO—$(CH_2)_n$—CO—X in which n is 2 to 14 and X is a natural or partially digested chitosan.

Yet in a further embodiment of the invention, R and $R_1$ are interchangeably CO—$(CH_2)_n$—CO—X in which n is 2 to 14 and X is selected from the group consisting of D-glucosamine, D-galactosamine, mannosamine, fucosamine, mycosamine and muramic acid and CO—$(CH_2)_n$—CO—X in which n is 2 to 14 and X is selected from the group consisting of asparagine, glutamine and lysine.

Preferred amino acid that can be used in accordance with the present invention include, without limitation, asparagine, glutamine and lysine.

In another embodiment of the invention, R and R1 are interchangeably CO—$(CH_2)_n$—CO—X in which n is 2 to 14 and X is a natural or partially digested chitosan and CO—$(CH_2)_n$—CO—X in which n is 3 to 8 and X is selected from the group consisting of asparagine, glutamine and lysine.

Still in accordance with the present invention, there is provided a polymeric compound comprising 2 to 100 units of D-glucosamine, each unit bearing a compound of formula II:

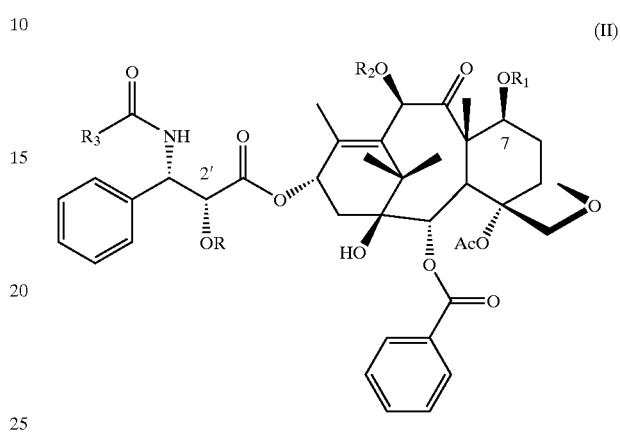

wherein $R_2$ is a hydrogen or acetyl and $R_3$ is phenyl or t-Butyloxy and wherein R and $R_1$ are interchangeably CO—$(CH_2)_n$—CO—X in which n is 2 to 14 and X is a bond attaching the compound of formula II to a nitrogen of the glucosamine and a hydrogen.

In one embodiment, R and $R_1$ are interchangeably CO—$(CH_2)_n$—CO—X in which n is 2 to 14 and X is a bond attaching the compound of formula II to a nitrogen of the glucosamine and CO—$(CH_2)_n$—CO—X in which n is 2 to 14 and X is selected from the group consisting of asparagine, glutamine and lysine.

In accordance with the present invention, there is further provided a chitosan derivative consisting of a natural or partially digested chitosan bearing one more units of the compound as defined above wherein X is a bond attaching the compound to a nitrogen of said chitosan and R1 is a hydrogen.

Sugars that can be used in accordance with the present invention include without limitation, glucose, mannose, galactose, arabinose, lactose, fructose, xylose, sucrose, fucose, raffinose, rhamnose, melibiose, stachyose and maltose.

In another embodiment of the invention, X can also be a mono-, di- or polysaccharide.

Also in accordance with the present invention, there is provided a polysaccharide consisting of 2 to 100 units of monosaccharide bearing 2 to 100 units of the compound as defined previously, wherein X is a bond attaching said compound to said polysaccharide.

In accordance with the present invention, there is also provided a method for the in vivo treatment or prophylaxis of skin cancer comprising the step of administering a therapeutically effective amount of a water-soluble paclitaxel and docetaxel derivatives as defined above to a patient in need of such a treatment.

For the purpose of the present invention the following terms are defined below.

The expression "amino sugar" is for example intended to mean without limitation any carbohydrate having an amino group attached thereon by a covalent bond.

DETAILED DESCRIPTION OF THE PREFERRED EMBODIMENT

To increase their solubility and their bioavailability within a cell, while preserving their cytotoxicity, in accordance with one embodiment of the present invention, there is provided new paclitaxel and docetaxel derivatives substituted at the 2' or/and 7 position of the paclitaxel and docetaxel molecules respectively.

In accordance with a preferred embodiment of the invention, there is provided new paclitaxel and docetaxel derivatives having the following formula:

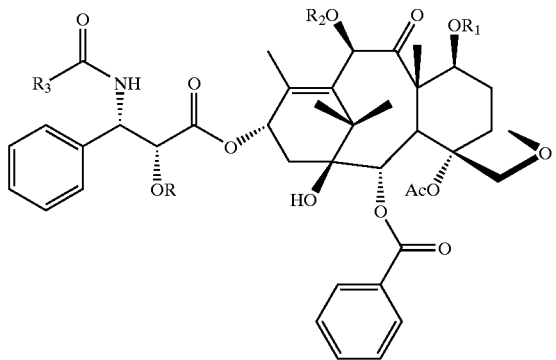

Wherein R and $R_1$, identical or different, are a hydrogen or CO—$(CH_2)_n$—CO—X in which n is 2 to 14 and X is a carbohydrate, an amino sugar or an amino acid and wherein $R_2$ is a hydrogen or acetyl and $R_3$ is phenyl (in the case of paclitaxel derivatives) or t-Butyloxy (in the case of docetaxel derivatives).

Synthesis of Derivatives

Synthesis of $C_2'$ Dioic Esters of Paclitaxel

In accordance with the present invention, dioic esters of paclitaxel were synthesized. To do this, 500 mg of paclitaxel were dissolved in pyridine and one gram of dioic acid anhydride was added. The solution was stirred for 3 hours at room temperature after which time the solvent was evaporated to dryness under vacuo. The residue was rinsed three times with 5 ml of water. The residue was then dissolved in 15 ml of methanol. The product was precipitated by the slow addition of 120 ml of water. The precipitate was collected on a sintered glass filter and dried. This procedure yielded about 450 mg of $C_2'$ dioyl paclitaxel.

Synthesis of $C_2'$ Dioyl-glucosamino Paclitaxel

The different $C_2'$ carbohydrate derivatives of paclitaxel were synthesized from the $C_2'$ dioic esters of paclitaxel synthesized above according to the present invention. To do this 400 mg of $C_2'$ dioyl paclitaxel was dissolved in 15 ml of acetonitrile and 50 mg of 1,1'-carbonyldiimidazole(CDI) was added. The solution was heated for 30 minutes at 45° C. Two hundred milligrams of an amino sugar such as glucosamine dissolved in 10 ml of dimethylsulfoxide:acetonitrile (1:1) was added slowly over a period of three hours. The solution was stirred overnight at room temperature. Solvents were evaporated to dryness under vacuo. The residue was rinsed three times with 3 ml of water and dissolved in 20 ml of methanol. The carbohydrate derivative was precipitated by the addition of three volume of water.

Synthesis of $C_2'C_7$ Dioic Esters of Paclitaxel

The $C_7$ hydroxyl group is less reactive than the $C_2'$ hydroxyl and in order to synthesize the $C_2'C_7$ diester, paclitaxel had to be heated in the presence of dimethylamino pyridine (DMAP). In accordance with the present invention, dioic diesters of paclitaxel were synthesized as described above. To do this, 500 mg of paclitaxel were dissolved in dimethylformamide and one gram of dioic acid anhydride was added with 40 mg of DMAP. The solution was stirred for 20 hours at 85° C. after which time the solvent was evaporated to dryness. The residue was rinsed three times with 5 ml of water and the residue was dissolved in 15 ml of methanol. The product was precipitated by the slow addition of 120 ml of water. The precipitate was collected on a sintered glass filter and dried. This procedure yielded about 450 mg of $C_2'C_7$ didioyl paclitaxel.

Synthesis of $C_2'C_7$ Glutaryl-glucosamino Paclitaxel

Different $C_2'C_7$ carbohydrate derivatives of paclitaxel such as diglutaryl diglucosamino paclitaxel were synthesized from the $C_2'C_7$ dioic diesters of paclitaxel according to the present invention. To do this, 400 mg of $C_2'C_7$ didioyl paclitaxel was dissolved in 15 ml of acetonitrile and 50 mg of 1,1'-carbonyldiimidazole(CDI) was added. The solution was heated for 30 minutes at 45° C. Two hundred milligrams of an amino sugar such as glucosamine dissolved in 10 ml of dimethylsulfoxide:acetonitrile (1:1) was added slowly over a period of three hours. The solution was stirred overnight at room temperature. Solvents were evaporated to dryness under vacuo. The residue was rinsed three times with 3 ml of water and dissolved in 20 ml of methanol. The carbohydrate derivative was precipitated by the addition of three volumes of water.

Synthesis of $C_7$ Dioic Esters of Paclitaxel

In accordance with the present invention $C_7$ dioic esters of paclitaxel were synthesized. To do this, 500 mg of paclitaxel were dissolved in pyridine and 150 mg of trichloethylchloroformate (Troc) was added. The solution was stirred for 20 hours at room temperature after which time the solvent was evaporated to dryness. The residue was rinsed three times with 5 ml of water and the residue was dissolved in 15 ml of methanol. The product was precipitated by the slow addition of 120 ml of water. The precipitate was collected on a sintered glass filter and dried. This procedure yielded about 450 mg of $C_2'$ Troc-paclitaxel.

The $C_7$ hydroxyl group is less reactive than the $C_2'$ hydroxyl and in order to synthesize the $C_7$ ester, $C_2'$ Troc paclitaxel had to be heated in the presence of dimethylamino pyridine (DMAP). To do this, 500 mg of $C_2'$ Troc paclitaxel were dissolved in dimethylformamide and one gram of dioic acid anhydride was added with 40 mg of DMAP. The solution was stirred for 20 hours at 85° C. after which time the solvent was evaporated to dryness. The residue was rinsed three times with 5 ml of water and the residue was dissolved in 15 ml of methanol. The product was precipitated by the slow addition of 120 ml of water. The precipitate was collected on a sintered glass filter and dried. This procedure yielded about 400 mg of $C_2'$ Troc-$C_7$ dioyl paclitaxel.

This product was then dissolved in 10 ml of a 10:1 mixture of methanol:glacial acetic acid and 100 mg of zinc powder was added. The solution was stirred two hours at room temperature and the solvent was evaporated to dryness. The residue was taken in 50 ml of dichoromethane and washed with 0.01N HCl, 0.01N sodium bicarbonate and water. The organic phase was dried with solid sodium sulfate and the organic phase was evaporated to dryness. The residue was taken in 15 ml of methanol and the C7 dioic ester derivative of paclitaxel was precipitated with water. The precipitate was filtered on a sintered glass filter and dried. This yielded about 300 mg of $C_7$ dioyl derivative of paclitaxel.

Synthesis of C7 Dioyl-glucosamino Paclitaxel

The different $C_7$ carbohydrate derivatives of paclitaxel were synthesized from the $C_7$ dioic esters of paclitaxel synthesized above according to the present invention. To do this, 300 mg of $C_7$ dioyl-paclitaxel was dissolved in 15 ml of acetonitrile and 50 mg of 1,1'-carbonyldiimidazole (CDI)

was added. The solution was heated for 30 minutes at 45° C. Two hundred milligrams of an aminosugar such as glucosamine dissolved in 10 ml of dimethylsulfoxide:acetonitrile (1:1) was added slowly over a period of three hours. The solution was stirred overnight at room temperature. Solvents were evaporated to dryness under vacuo. The residue was rinsed three times with 3 ml of water and dissolved in 20 ml of methanol. The carbohydrate derivative was precipitated by the addition of three volumes of water.

Synthesis of Paclitaxel Amino Sugar Polymer Conjugate

In accordance with the present invention, carbohydrate polymers were used as carriers for paclitaxel. To do this, 100 mg of paclitaxel were dissolved in pyridine and one gram of dioic acid anhydride was added. The solution was stirred for 3 hours at room temperature after which time the solvent was evaporated to dryness. The residue was rinsed three times with 5 ml of water and the residue was dissolved in 15 ml of methanol. The product was precipitated by the slow addition of 120 ml of water. The precipitate was collected on a sintered glass filter and dried. This procedure yielded about 90 mg of $C_2'$ dioyl paclitaxel.

50 mg of $C_2'$ dioyl paclitaxel was dissolved in 15 ml of acetonitrile and 50 mg of 1,1'-carbonyldiimidazole (CDI) was added. The solution was heated for 30 minutes at 45° C.

The solution was cooled to room temperature and slowly added to 50 ml of dimethylsulfoxide:acetonitrile (2:1) containing two grams of an amino sugar polymer such as chitosan. The solution was stirred 20 hours at room temperature and the solvent was evaporated to dryness. The residue was then washed three times with 20 ml of methanol and dried under vacuo. This yielded about two grams of conjugate of paclitaxel with a carbohydrate polymer such as chitosan in which the $C_2'$ side chain is strongly bound to the polymer by an amido bond while the paclitaxel moiety is bound to the latter side chain by an ester linkage.

The present invention is more readily understood by referring to the following examples, which are given to illustrate the invention rather than to limit the scope.

EXAMPLE 1

Synthesis of $C_2'$ Glutaryl Paclitaxel

One gram of paclitaxel was dissolved in 25 ml of pyridine and 1.74 grams of glutaric anhydride was added slowly. The solution was stirred at room temperature for three hours and the solvent was evaporated to dryness. The residue is rinsed three times with 5 ml of water and dissolved in 12 ml of methanol. The product was precipitated with eight volumes of water. The white product was dried under vacuo. This yielded 700 mg of $C_2'$ glutaryl paclitaxel.

The product was fluorescent under UV light, gave a positive reaction with vanillin and gave a single spot at an rf of 0.50 on thin layer chromatography on silica gel as compared to 0.67 for paclitaxel.

EXAMPLE 2

Synthesis of C2' Glutaryglucosamino Paclitaxel

One hundred (100) mg of $C_2'$ glutaryl paclitaxel was dissolved in 4 ml of acetonitrile. Thirty (30) mg of carboxydiimidazole (CDI) in 2 ml of acetonitrile was added. The solution was heated at 45° C. for 30 minutes. After cooling to room temperature 110 mg of glucosamine in 2 ml of dimethylsulfoxide was added. The solution was stirred at room temperature for 20 hours and the solvent was evaporated to dryness. The residue was taken in 3 ml of methanol and the product was precipitated with eight volumes of water. This yielded 46 mg of glutarylglucosamino paclitaxel. The product was fluorescent under Ultraviolet light, reacted with vanillin to give a yellow spot and gave a single spot at an rf of 0.05 on thin layer chromatography on silica gel as compared to 0.67 for paclitaxel. The product has a tendency to gelify in the presence of water.

EXAMPLE 3

Synthesis of C2'C7 Diglutaryl Paclitaxel

One gram of paclitaxel was dissolved in 12 ml of dimethylformamide with 1.74 grams of glutaric anhydride and 36 mg of dimethylaminopyridine (DMAP). The solution was stirred at 85° C. for 20 hours and the solvent was evaporated to dryness. The residue is rinsed three times with 5 ml of water and taken in 20 ml of acetone. The product was precipitated with eight volumes of water. The white product was dried under vacuo. This yielded 500 mg of $C_2'C_7$ diglutaryl paclitaxel.

The product was fluorescent under UV light, gave a positive reaction with vanillin and gave a single spot at an rf of 0.55 on thin layer chromatography on silica gel as compared to 0.67 for paclitaxel.

EXAMPLE 4

Synthesis of C2'C7 di Glutaryglucosamino Paclitaxel

One hundred (100) mg of $C_2'C_7$ diglutaryl paclitaxel was dissolved in 4 ml of acetonitrile and 30 mg of carboxydiimidazole (CDI) in 2 ml of acetonitrile was added. The solution was heated at 45° C. for 30 minutes. After cooling to room temperature 110 mg of glucosamine in 2 ml of dimethylsulfoxide was added. The solution was stirred at room temperature for 20 hours and the solvent was evaporated to dryness. The residue was taken in 3 ml of methanol and the product was precipitated with eight volumes of water. This yielded 50 mg of diglutarylglucosamino paclitaxel. The product was fluorescent under Ultraviolet light, reacted with vanillin to give a yellow spot and gave a single spot at an rf of 0.05 on thin layer chromatography on silica gel as compared to 0.67 for paclitaxel. The product has a tendency to gelify in the presence of water.

EXAMPLE 5

Synthesis of C7 Glutaryl Paclitaxel 875 mg of paclitaxel was dissolved in 6 ml of pyridine and 40 ml of dichloromethane. The solution was cooled at −20° C. Three hundred microliters of trichloroethylchloroformate (Troc) (at −20° C.) was added by portions of 100 microliters and the solution was kept at −20°C. for two hours. An additional 100 microliters of Troc was added and the solution was stirred at room temperature for 20 hours. The solvent was evaporated to dryness. The residue was dissolved in 10 ml of dimethylformamide with 1.36 g of glutaric anhydride and 40 mg of dimethylaminopyridine. The solution was stirred at 85° C. for 20 hours. The product was precipitated with 10 volumes of water. The white precipitate was collected on a sintered glass filter and dried. The dried product was then dissolved in 20 ml of methanol:acetic acid (9:1) and 0.5 g of zinc powder was added. The solution was stirred at room temperature for 30 minutes. Zinc was filtered and the filtrate was evaporated to a volume of about 2 ml. 70 ml of dichloromethane was added and the solution was washed twice with 30 ml of 0.01N HCl, once with 30 ml of sodium bicarbonate and once with 50 ml of water. The organic phase was dried with anhydrous sodium sulfate, filtered and evaporated to dryness. This yielded 620 mg of a $C_7$-glutaryl paclitaxel

EXAMPLE 6

Synthesis of C7 Glutarylglucosamino Paclitaxel

One hundred (100) mg of $C_7$ glutaryl paclitaxel was dissolved in 4 ml of acetonitrile and 30 mg of carboxydi-imidazole (CDI) in 2 ml of acetonitrile was added. The solution was heated at 45° C. for 30 minutes. After cooling to room temperature 110 mg of glucosamine in 2 ml of dimethylsulfoxide was added. The solution was stirred at room temperature for 20 hours and the solvent was evaporated to dryness. The residue was taken in 3 ml of methanol and the product was precipitated with eight volumes of water. This yielded 70 mg of $C_7$ glutarylglucosamino paclitaxel. The product was fluorescent under Ultraviolet light, reacted with vanillin to give a yellow spot and gave a single spot at an rf of 0.05 on thin layer chromatography on silica gel as compared to 0.67 for paclitaxel. The product has a tendency to gelify in the presence of water.

EXAMPLE 7

Synthesis of C2' Glutarylpaclitaxel Chitosan Conjugate

One gram of paclitaxel was dissolved in 25 ml of pyridine and 1.74 grams of glutaric anhydride was added slowly. The solution was stirred at room temperature for three hours and the solvent was evaporated to dryness. The residue is rinsed three times with 5 ml of water and taken in 12 ml of methanol. The product was precipitated with eight volumes of water. The $C_2$' glutaryl paclitaxel was dried under vacuo. The precipitate was collected on a sintered glass filter and dried.

50 mg of $C_2$' glutaryl paclitaxel was dissolved in 15 ml of acetonitrile and 50 mg of 1,1'-carbonyldiimidazole (CDI) was added. The solution was heated for 30 minutes at 45° C.

The solution was cooled to room temperature and slowly added to 50 ml of dimethylsulfoxide:acetonitrile (2:1) containing two grams of chitosan. The solution was stirred 20 hours at room temperature and the solvent was evaporated to dryness. The residue was then washed three times with 20 ml of methanol and dried under vacuo. This yielded about two grams of $C_2$' glutaryl paclitaxel chitosan conjugate in which the $C_2$' side chain of paclitaxel is strongly bound to the polymer by an amido bond while the paclitaxel moiety is bound to the glutaryl side chain by an ester linkage.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:
1. A compound of Formula I:

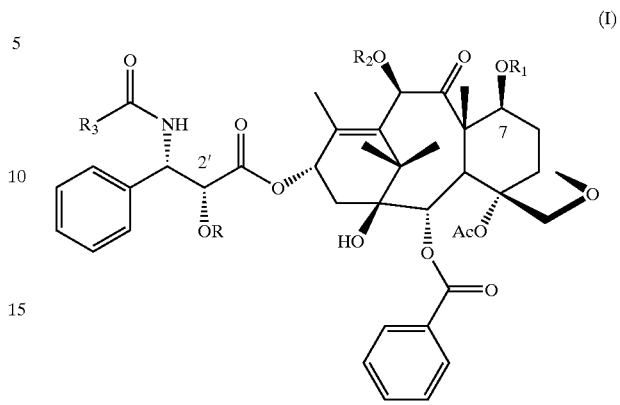

or a salt thereof, wherein $R_2$ is a hydrogen or acetyl and $R_3$ is phenyl or t-Butyloxy and wherein R and $R_1$, identical or different, are independently a hydrogen or CO—$(CH_2)_n$—CO—X in which n is 2 to 14 and X is an amino sugar chitosan mycosamine, myramic acid, monosaccharide, a disaccharide, a polysaccharide or an amino acid.

2. The compound of claim 1, wherein R is a hydrogen and $R_1$ is CO—$(CH_2)_n$—CO—X in which n is 2 to 14 and X is selected from the group consisting of D-glucosamine, D-galactosamine, mannosamine, fucosamine, lactosamine, mycosamine and muramic acid.

3. The compound of claim 1, wherein $R_1$ is a hydrogen and R is CO—$(CH_2)_n$—CO—X in which n is 2 to 14 and X is selected from the group consisting of D-glucosamine, D-galactosamine, mannosamine, fucosamine, lactosamine, mycosamine and muramic acid.

4. The compound of claim 1, wherein R and $R_1$, identical, are each CO—$(CH_2)_n$—CO—X in which n is 2 to 14 and X is selected from the group consisting of D-glucosamine, D-galactosamine, mannosamine, fucosamine, lactosamine, mycosamine and muramic acid.

5. The compound of claim 1, wherein R is a hydrogen and $R_1$ is CO—$(CH_2)_n$—CO—X in which n is 2 to 14 and X is a natural or synthetic polymer of amino sugars consisting of 2 to 100 units of D-glucosamine.

6. The compound of claim 1, wherein $R_1$ is a hydrogen and R is CO—$(CH_2)_n$—CO—X in which n is 2 to 14 and X is a natural or synthetic polymer of amino sugars consisting of 2 to 100 units of D-glucosamine.

7. The compound of claim 1, wherein R and $R_1$ are each CO—$(CH_2)_n$—CO—X in which n is 2 to 14 and X is a natural or synthetic polymer of amino sugars consisting of 2 to 100 units of D-glucosamine.

8. The compound of claim 7, wherein the polymer of same amino sugar is identical on R and $R_1$.

9. The compound of claim 1, wherein R is a hydrogen and $R_1$ is CO—$(CH_2)_n$—CO—X in which n is 2 to 14 and X is a natural or partially digested chitosan.

10. The compound of claim 1, wherein $R_1$ is a hydrogen and R is CO—$(CH_2)_n$—CO—X in which n is 2 to 14 and X is a natural or partially digested chitosan.

11. The compound of claim 1, wherein R and $R_1$, identical, are each CO—$(CH_2)_n$—CO—X in which n is 2 to 14 and X is a natural or partially digested chitosan.

12. The compound of claim 1, wherein R is CO—(CH$_2$)$_n$—CO—X in which n is 2 to 14 and X is selected from the group consisting of D-glucosamine, D-galactosamine, mannosamine, fucosamine, mycosamine and muramic acid and R$_1$ is CO—(CH$_2$)$_n$—CO—X in which n is 2 to 14 and X is selected from the group consisting of asparagine, glutamine and lysine.

13. The compound of claim 1, wherein R is CO—(CH$_2$)$_n$—CO—X in which n is 2 to 14 and X is selected from the group consisting of asparagine, glutamine and lysine and R1 is CO—(CH$_2$)$_n$—CO—X in which n is 2 to 14 and X is selected from the group consisting of D-glucosamine, D-galactosamine, mannosamine, fucosamine, lactosamine, mycosamine and muramic acid.

14. The compound of claim 1, wherein R is H and R$_1$ is CO—(CH$_2$)$_n$—CO—X in which n is 2 to 14 and X is selected from the group consisting of asparagine, glutamine and lysine.

15. The compound of claim 1, wherein R is CO—(CH$_2$)$_n$—CO—X in which n is 2 to 14 and X is a natural or synthetic polymer of an amino sugar consisting of 2 to 100 units of D-glucosamine and R$_1$ is CO—(CH$_2$)$_n$—CO—X in which n is 2 to 14 and X is selected from the group consisting of asparagine, glutamine and lysine.

16. The compound of claim 1, wherein R is CO—(CH$_2$)$_n$—CO—X in which n is 2 to 14 and X is selected from the group consisting of asparagine, glutamine and lysine and R$_1$ is CO—(CH$_2$)$_n$—CO—X in which n is 2 to 14 and X is a natural or synthetic polymer of an amino sugar consisting of 2 to 100 units of D-glucosamine.

17. The compound of claim 1, wherein R is CO—(CH$_2$)$_n$—CO—X in which n is 2 to 14 and X is a natural or partially digested chitosan and R$_1$ is CO—(CH$_2$)$_n$—CO—X in which n is 3 to 8 and X is selected from the group consisting of asparagine, glutamine and lysine.

18. The compound of claim 1, wherein R is CO—(CH$_2$)$_n$—CO—X in which n is 2 to 14 and X is selected from the group consisting of asparagine, glutamine and lysine and R$_1$ is CO—(CH$_2$)$_n$—CO—X in which n is 2 to 14 and X is a natural or partially digested chitosan.

19. A polymeric compound having 2 to 100 units of D-glucosamine, each unit having a compound of formula II:

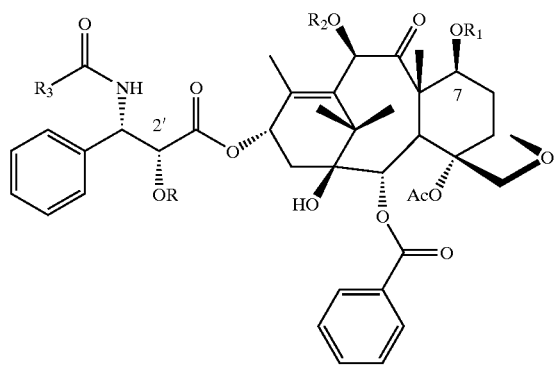

(II)

wherein R$_2$ is a hydrogen or acetyl and R$_3$ is phenyl or t-Butyloxy and wherein R is CO—(CH$_2$)$_n$—CO—X in which n is 2 to 14 and X is a bond attaching the compound of formula II to a nitrogen of the glucosamine and R$_1$ is a hydrogen.

20. A polymeric compound having 2 to 100 units of D-glucosamine, each unit having a compound of formula II:

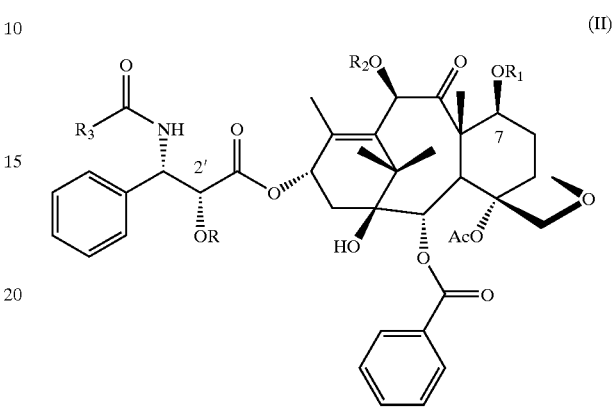

(II)

wherein R$_2$ is a hydrogen or acetyl and R$_3$ is phenyl or t-Butyloxy and wherein R is a hydrogen and R$_1$ is CO—(CH$_2$)$_n$—CO—X in which n is 2 to 14 and X is a bond attaching the compound of formula II to a nitrogen of the glucosamine.

21. A polymeric compound having 2 to 100 units of D-glucosamine, each unit having a compound of formula II:

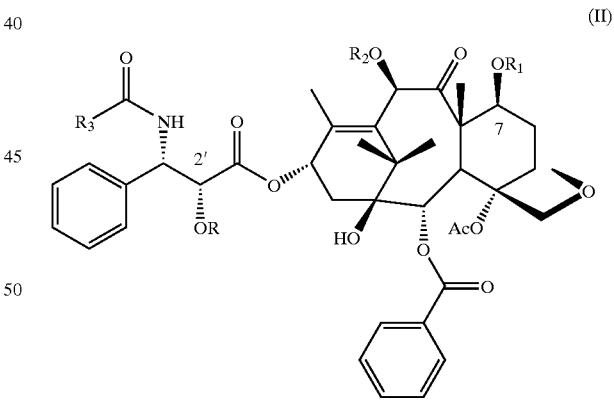

(II)

wherein R$_2$ is a hydrogen or acetyl and R$_3$ is phenyl or t-Butyloxy and wherein R is CO—(CH$_2$)$_n$—CO—X in which n is 2 to 14 and X is a bond attaching the compound of formula II to a nitrogen of the glucosamine and R$_1$ is CO—(CH2)n-CO—X in which n is 2 to 14 and X is selected from the group consisting of asparagine, glutamine and lysine.

22. A polymeric compound having 2 to 100 units of D-glucosamine, each unit having a compound of formula II:

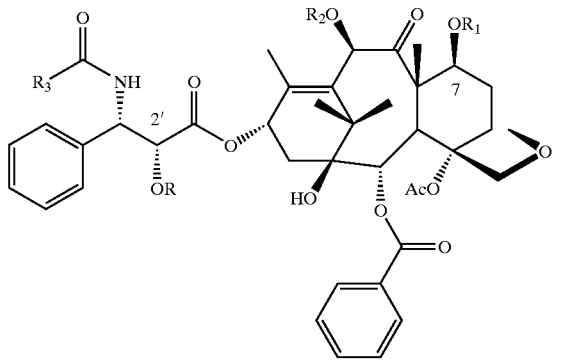

(II)

wherein $R_2$ is a hydrogen or acetyl and $R_3$ is phenyl or t-Butyloxy and wherein R is CO—$(CH_2)_n$—CO—X in which n is 2 to 14 and X is selected from the group consisting of asparagine, glutamine and lysine and $R_1$ is CO—$(CH_2)_n$—CO—X in which n is 2 to 14 and X is a bond attaching the compound of formula II to a nitrogen of the glucosamine.

23. A chitosan derivative consisting of a natural or partially digested chitosan having one more units of the compound of claim 1 wherein $R_2$ is a hydrogen or acetyl and R3 is phenyl or t-Butyloxy and wherein R is CO—$(CH_2)_n$—CO—X in which n is 2 to 14 and X is a bond attaching the compound of claim 1 to a nitrogen of said chitosan and $R_1$ is a hydrogen.

24. A chitosan derivative consisting of a natural or partially digested chitosan having one more units of the compound of claim 1 wherein $R_2$ is a hydrogen or acetyl and $R_3$ is phenyl or t-Butyloxy and wherein R is a hydrogen and $R_1$ is CO—$(CH_2)_n$—CO—X in which n is 2 to 14 and X is a bond attaching the compound of claim 1 to a nitrogen of said chitosan.

25. A chitosan derivative consisting of a natural or partially digested chitosan having one more units of the compound of claim 1 wherein $R_2$ is a hydrogen or acetyl and $R_3$ is phenyl or t-Butyloxy and wherein R is CO—$(CH_2)_n$—CO—X in which n is 2 to 14 and X is a bond attaching the compound of claim 1 to a nitrogen of said chitosan and $R_1$ is CO—$(CH_2)_n$—CO—X in which n is 2 to 14 and X is selected from the group consisting of asparagine, glutamine and lysine.

26. A chitosan derivative consisting of a natural or partially digested chitosan having one more units of the compound of claim 1 wherein $R_2$ is a hydrogen or acetyl and $R_3$ is phenyl or t-Butyloxy and wherein R is CO—$(CH_2)_n$—CO—X in which n is 2 to 14 and X is selected from the group consisting of asparagine, glutamine and lysine and $R_1$ is CO—$(CH_2)_n$—CO—X in which n is 2 to 14 and X is a bond attaching the compound of claim 1 to a nitrogen of said chitosan.

27. The compound of claim 1, wherein R is a hydrogen and $R_1$ is CO—$(CH_2)_n$—CO—X in which n is 2 to 14 and X is selected from the group of sugars consisting of glucose, mannose, galactose, arabinose, lactose, fructose, xylose, sucrose, fucose, raffinose, rhamnose, melibiose, stachyose and maltose.

28. The compound of claim 1, wherein $R_1$ is a hydrogen and R is CO—$(CH_2)_n$—CO—X in which n is 2 to 14 and X is selected from the group of sugars consisting of glucose, mannose, galactose, arabinose, lactose, fructose, xylose, sucrose, fucose, raffinose, rhamnose, melibiose, stachyose and maltose.

29. The compound of claim 1, wherein R and $R_1$, identical, are each CO—$(CH2)n$-CO—X in which n is 2 to 14 and X is selected from the group of sugars consisting of glucose, mannose, galactose, arabinose, lactose, fructose, xylose, sucrose, fucose, raffinose, rhamnose, melibiose, stachyose and maltose.

30. The compound of claim 1, wherein R is a hydrogen and $R_1$ is CO—$(CH_2)_n$—CO—X in which n is 2 to 14 and X is a mono-, di- or polysaccharide.

31. The compound of claim 1, wherein $R_1$ is a hydrogen and R is CO—$(CH_2)_n$—CO—X in which n is 2 to 14 and X is a mono-, di- or polysaccharide.

32. The compound of claim 1, wherein R and $R_1$, identical are both CO—$(CH_2)_n$—CO—X in which n is 2 to 14 and X is a mono-, di- or polysaccharide.

33. The compound of claim 1, wherein R is CO—$(CH_2)_n$—CO—X in which n is 2 to 14 and X is selected from the group of sugars consisting of glucose, mannose, galactose, arabinose, lactose, fructose, xylose, sucrose, fucose, raffinose, rhamnose, melibiose, stachyose and maltose and $R_1$ is CO—$(CH_2)_n$—CO—X in which n is 2 to 14 and X is selected from the group consisting of asparagine, glutamine and lysine.

34. The compound of claim 1, wherein R is CO—$(CH_2)_n$—CO—X in which n is 2 to 14 and X is selected from the group consisting of asparagine, glutamine and lysine and $R_1$ is CO—$(CH_2)_n$—CO—X in which n is 2 to 14 and X is selected from the group of sugars consisting of glucose, mannose, galactose, arabinose, lactose, fructose, xylose, sucrose, fucose, raffinose, rhamnose, melibiose, stachyose and maltose.

35. The compound of claim 1, wherein R is CO—$(CH_2)_n$—CO—X in which n is 2 to 14 and X is a mono-, di- or polysaccharide and $R_1$ is CO—$(CH_2)_n$—CO—X in which n is 2 to 14 and X is selected from the group consisting of asparagine, glutamine and lysine.

36. The compound of claim 1, wherein R is CO—$(CH_2)_n$—CO—X in which n is 2 to 14 and X is selected from the group consisting of asparagine, glutamine and lysine and $R_1$ is CO—$(CH_2)_n$—CO—X in which n is 2 to 14 and X is a mono-, di- or polysaccharide.

37. A polysaccharide consisting of 2 to 100 units of monosaccharide having 2 to 100 units of the compound of claim 1, wherein $R_1$ is CO—$(CH_2)_n$—CO—X in which n is 2 to 14 and X is a bond attaching said compound to said polysaccharide.

38. A polysaccharide consisting of 2 to 100 units of monosaccharide having 2 to 100 units of the compound of claim 1, wherein R is a hydrogen and $R_1$ is CO—$(CH_2)_n$—CO—X in which n is 2 to 14 and X is a bond attaching said compound to said polysaccharide.

39. A polysaccharide consisting of 2 to 100 units of monosaccharide having 2 to 100 units of the compound of claim 1, wherein R is CO—$(CH_2)_n$—CO—X in which n is 3, to 8 and X is a bond attaching said compound to said polysaccharide and $R_1$ is CO—$(CH_2)_n$—CO—X in which n is 2 to 14 and X is selected from the group consisting of asparagine, glutamine and lysine.

40. A polysaccharide consisting of 2 to 100 units of monosaccharide having 2 to 100 units of the compound of claim 1, wherein R is CO—$(CH_2)_n$—CO—X in which n is 3 to 8 and X is selected from the group consisting of asparagine, glutamine and lysine and $R_1$ is CO—$(CH_2)_n$—CO—X in which n is 2 to 14 and X is a bond attaching said compound to said polysaccharide.

41. A method for the in vivo treatment or prophylaxis of skin cancer comprising the step of administering a therapeutically effective amount of a compound as defined in claim 1 to a patient in need of such a treatment.

* * * * *